United States Patent [19]

Sawa et al.

[11] 4,122,277

[45] Oct. 24, 1978

[54] 2-TOLYL-4,5-DIHYDROXYMETHYL IMIDAZOLE

[75] Inventors: Natsuo Sawa, Nakatado; Kyoko Gohda, Kanonji, both of Japan

[73] Assignee: Shikoku Chemicals Corporation, Japan

[21] Appl. No.: 802,972

[22] Filed: Jun. 2, 1977

Related U.S. Application Data

[62] Division of Ser. No. 679,663, Apr. 23, 1976.

[51] Int. Cl.$^2$ ............................................. C07D 233/64
[52] U.S. Cl. .................................................. 548/342
[58] Field of Search ........................................ 548/342

[56] References Cited

FOREIGN PATENT DOCUMENTS

2,528,640  1/1976  Fed. Rep. of Germany ............ 548/342
42-1,546   1/1964  Japan ..................................... 548/342

OTHER PUBLICATIONS

Dziuron et al., I Arch. Pharmaz. 1973, vol. 306, pp. 347–350.
Dziuron et al., II Arch. Pharmaz. 1974, vol. 307, pp. 89–95.
Imbach et al., Bulletin Soc. Chim. (France) 1971, pp. 1052–1060.
Cornforth et al., J. Chem. Soc. 1948, pp. 731–735.
Perez, Chem. Abst. 1953, vol. 47, col. 2764.

*Primary Examiner*—Natalie Trousof
*Attorney, Agent, or Firm*—Wenderoth, Lind & Ponack

[57] ABSTRACT

A process for producing C-methylol imidazoles which comprises reacting imidazole compounds containing an aryl group at the 2-position with formaldehyde in a reaction medium having a pH of at least 7 whereby the formaldehyde adds to the carbon atom of the imidazole ring. The products are either monomethylol imidazoles or dimethlol imidazoles depending upon the starting imidazole compounds. Most of the C-methylol imidazoles thus obtained are new compounds.

1 Claim, No Drawings

2-TOLYL-4,5-DIHYDROXYMETHYL IMIDAZOLE

This application is a division of application Ser. No. 679,663, filed Apr. 23, 1976.

FIELD OF THE INVENTION

This invention relates to novel processes for preparing imidazole compounds containing a 2-aryl group and a hydroxymethyl group bonded to the carbon atom on the imidazole ring by reacting imidazoles containing an aryl group at the 2-position with formaldehyde, and to novel imidazole compounds obtained thereby.

BACKGROUND OF THE INVENTION

The reaction of imidazoles containing an aryl group at the 2-position with formaldehyde was reported by J. W. Cornforth and H. T. Huang in Journal of the Chemical Society 1948, page 733, and it was stated that the reaction was unsuccessful.

We have now found that when an imidazole not containing an aryl group at the 2-position was reacted with formaldehyde, the formaldehyde adds to the imino nitrogen atom at the 1-position of the imidazole ring to give unstable 1-hydroxymethylimidazole (i.e., N-methylol imidazole), but that an imidazole containing an aryl group at the 2-position reacts with formaldehyde to afford stable C-methylol imidazole in which the formaldehyde adds to the carbon atom of the imidazole ring.

The reaction between the imidazole not containing an aryl group at the 2-position and formaldehyde is schematically shown as follows:

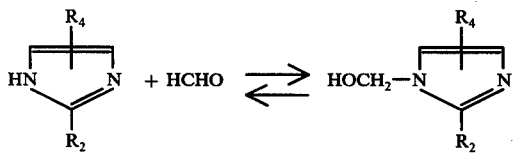

wherein $R_2$ represents, for example, a hydrogen atom or an alkyl or benzyl group, and $R_4$ represents, for example, a hydrogen atom or an alkyl or phenyl group.

As shown above, in the reaction of the imidazole not containing an aryl group at the 2-position with formaldehyde, the formaldehyde adds to the NH group at the 1-position to give an N-methylol derivative. The N-methylol derivative is unstable, and when allowed to stand in air, spontaneously decomposes to the imidazole while releasing formaldehyde. Furthermore, it decomposes by the action of water (or acidic water) to afford an aqueous solution of formaldehyde and the imidazole. For example, attempt to acetylate its hydroxyl group with acetic anhydride fails to give the desired acetyl ester because decomposition occurs first. Only the reaction of it with phenyl isocyanate can give stable phenyl urethane.

Examples of the N-methylol derivative are as follows:

1-Methylol imidazole:
  Melting point, 58°–59° C. (acetone),
  $\nu$C-O, 1065 cm$^{-1}$
  Melting point of phenylurethane prepared therefrom, 167°–168° C. (acetone),
1-Methylol-2-methyl imidazole:
  Melting point, 95.5°–96.5° C. (acetone),
  $\nu$C-O, 1065 cm$^{-1}$
  Melting point of phenylurethane prepared therefrom, 161°–162° C. (benzene),
1-Methylol-2-ethyl imidazole:
  Melting point, 73°–74° C. (acetone),
  $\nu$C-O 1048, 1075 cm$^{-1}$,
  Melting point of phenylurethane prepared therefrom, 141°–142° C. (benzene),
1-Methylol-2,4(5)-dimethyl imidazole:
  Melting point 108°–109° C. (acetone),
  $\nu$C-O, 1070 cm$^{-1}$,
  Melting point of phenylurethane prepared therefrom, 155°–156° C. (acetonitrile),
1-Methylol-2-ethyl-4(5)-methyl imidazole:
  Melting point, 85°–86° C. (acetone),
  $\nu$C-O, 1060 cm$^{-1}$,
  Melting point of phenylurethane prepared therefrom, 129.5°–130.5° C. (acetone).

In view of the above experimental results, it is surprising that when an imidazole containing an aryl group at the 2-posttion is reacted with formaldehyde in a reaction medium having a pH of at least 7, the formaldehyde adds to the carbon atom of the imidazole ring to afford C-methylol imidazole, and the resulting C-methylol imidazole is a very stable compound.

SUMMARY OF THE INVENTION

According to the present invention, there is provided a process for preparing a compound (to be referred to as a dimethylol imidazole) of the formula

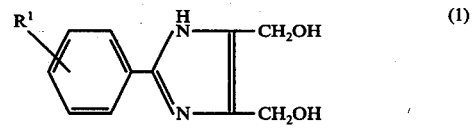

wherein
R' represents a hydrogen atom or an alkyl group containing 1 to 4 carbon atoms, which comprises reacting a 2-arylimidazole of the formula

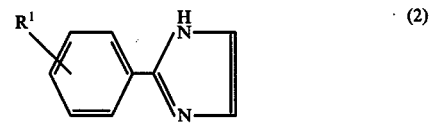

wherein R' is the same as defined above, with at least 2 moles, per mole of the 2-arylimidazole, of formaldehyde in a reaction medium having a pH of at least 7.

The dimethylol imidazoles of formula (1) obtained by the above process are novel compounds.

The invention also provides a process for preparing a compound (to be referred to as a monomethylol imidazole) of the formula

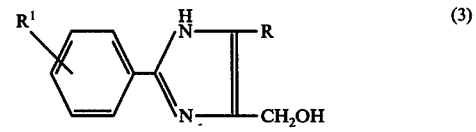

wherein R represents an alkyl group containing 1 to 4 carbon atoms or a benzyl group, and R' represents a hydrogen atom or an alkyl group containing 1 to 4 carbon atoms, which comprises reacting a 2-arylimidazole of the formula

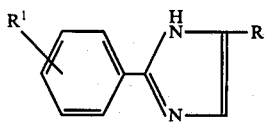
(4)

wherein R and R' are the same as defined above, with at least 1 mole, per mole of the 2-aryl imidazole, of formaldehyde in a reaction medium having a pH of at least 7.

The monomethylol imidazoles of the formula

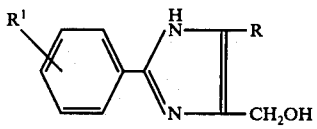
(3)

wherein R represents an alkyl group containing 1 to 4 carbon atoms or a benzyl group, and R' represents a hydrogen atom or an alkyl group containing 1 to 4 carbon atoms, with the proviso that a compound of the above formula in which R' is a hydrogen atom and R is a methyl group is excluded from the above definition, obtained by the above method are novel compounds.

The compound of formula (3) wherein R' is hydrogen and R is methyl was synthesized by the reaction of α-diketone with benzamidine, as reported by J. W. Cornforth and H. T. Huang in Journal of the Chemical Society 1948, pages 731 to 733. They reported that an attempt to synthesize this compound directly by reacting a 2-arylimidazole with formaldehyde failed.

DETAILED DESCRIPTION OF THE INVENTION

The imidazole compound as a starting material in the process of this invention is obtained by dehydrogenating imidazoline (which is prepared from a 1,2-aliphatic diamine and nitrile by the processes disclosed in U.S. Pat. No. 3,210,371 and Japanese patent publication No. 1548/67) by the process disclosed in Japanese patent publication No. 26405/64.

It is important that in the process of this invention, the reaction should be performed in a reaction medium having a pH of at least 7, preferably 7 to 13. When the reaction is carried out in an acidic reaction system, a viscous substance difficult to purify forms instead of the desired product which is crystalline. The reaction temperature is not critical in particular, but generally, the reaction is carried out preferably at 40° to 200° C. The reaction pressure is neither critical, and the reaction can be carried out at atmospheric pressure or at an elevated pressure.

The reaction in accordance with this invention can be performed even in the absence of a catalyst. But in order to perform the reaction smoothly within short periods of time, it is preferred to use catalysts. Basic substances are suitable catalysts for this purpose. Organic basic substances include, for example, quaternary ammonium hydroxides such as benzyltrimethyl ammonium hydroxide (Triton-B), and tertiary amines such as triethylamine or imidazole compounds, and alkali metal salts of imidazole. The starting 2-arylimidazole itself has basicity, and exhibits a catalytic activity. Inorganic basic substances include, for example, hydroxides or carbonates of alkali metals or alkaline earth metals. Specific examples are lithium hydroxide, sodium hydroxide, potassium hydroxide, lithium carbonate, sodium carbonate, potassium carbonate, calcium hydroxide, barium hydroxide, calcium carbonate, and barium carbonate. Of these, the sodium hydroxide, potassium hydroxide, sodium carbonate, and potassium carbonate are especially preferred. The calcium or barium type catalysts are sparingly soluble in water, and are not preferred because their removal is complicated.

Generally, it is preferred to use the catalyst in an amount of not more than 0.5 equivalent per mole of the 2-arylimidazole. Where sodium hydroxide or potassium hydroxide is used as the catalyst, it promotes the Cannizzaro reaction, and therefore, should not be used in an amount of more than 0.5 mole.

In the performance of the process of this invention, formaldehyde is used in an amount exceeding the equivalent weight required for the reaction. Specifically, where it is desired to obtain dimethylol imidazoles as a final product, the amount of formaldehyde is at least 2 moles, preferably 2 to 3 moles, per mole of the 2-arylimidazole. Where monomethylol imidazoles are desired, formaldehyde is used in an amount of at least 1 mole, preferably 1 to 1.5 moles, per mole of the 2-arylimidazole. In either cases, the use of more than 1.5 times the equivalent weight of formaldehyde is not preferred because not only is it uneconomical, but also it may cause side-reactions.

The reaction in accordance with the present invention can be performed either in an aqueous medium or in an organic solvent medium. When the reaction is performed in aqueous media, a commercially available 37% aqueous solution of formaldehyde (formalin) may be used as such or after being diluted to 2 to 3 times the original volume. Furthermore, paraformaldehyde may be used as a source of formaldehyde, and water added prior to use. However, since the paraformaldehyde is higher in cost than formalin, this method has no significant advantage. Instead of the formalin, paraformaldehyde and an organic solvent may be used together. The organic solvent used for this purpose is preferably an alcohol solvent which well disssolves the reaction reagents but sparingly dissolves the final product. Suitable alcohol solvents are, for example, methanol, ethanol, and methyl cellosolve (ethylene glycol monomethyl ether).

In one preferred embodiment of the process of this invention, a 2-arylimidazole, an aqueous solution of formaldehyde (containing formaldehyde in an amount more than the equivalent weight required for the reaction with regard to the 2-arylimidazole), and a catalyst are heated with stirring in a reaction vessel equipped with a stirrer and a reflux condenser, and the reaction is carried out under reflux at about 100° C. for 10 minutes to several hours. The starting 2-arylimidazole first dissolves almost uniformly in the reaction system, and then, the desired C-methylol derivative precipitates from the reaction system. This reaction is a mild exothermic reaction, but in order to maintain the reaction system at about 100° C., suitable temperature control is required. For this purpose, the formaldehyde may be added portionwise to the reaction system.

The resulting C-methylol derivative is purified by a conventional method. Specifically, the crystals in the reaction mixture after the reaction are collected by filtration, washed with water, dried, and then recrystallized.

Since the dimethylol imidazole and monomethylol imidazoles obtained by the present invention contain a tertiary nitrogen atom and a hydroxyl group, they are useful in a wide range of applications, for example, as curing agents for epoxides, dyeability improvers for polymers, additives to formaldehyde resins, and raw materials for ion-exchanger resins.

The following Examples illustrate the present invention. The compounds in these examples were identified by infrared spectroscopy, nuclear magnetic resonance spectroscopy, mass spectrometry, and elemental analysis.

EXAMPLE 1

A reaction vessel equipped with a stirrer and a reflux condenser was charged with 29 g (0.2 mole) of 2-phenylimidazole, 50 ml. (0.6 mole) of 37% formalin and 5.6 g (0.1 mole) of potassium hydroxide, and with stirring, they were heated to about 100° C. The contents instantly dissolved, and upon boiling which began after a while, crystals began to precipitate. After a lapse of 30 minutes from the beginning of heating, the contents were cooled, and the crystals were collected by filtration. The crystals collected were boiled together with 100 ml of water and cooled, and then the crystals were again collected by filtration. The crystals so collected were boiled with 50 ml of methanol, cooled, collected by filtration, and dried to afford 2-phenyl-4,5-dihydroxymethyl imidazole as a final product in a yield of 90%.

The thin-layer chromatography (cellulose, n-BuOH: AcOH:W = 4:1:2) of the crystals gave only one spot at $R_f = 0.7$.

The product was of the following formula

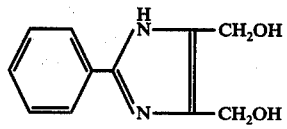

and had a melting point of 223° to 225° C. (decomp.) (methyl cellosolve). It was basic, readily soluble in an aqueous solution of hydrochloric acid, sparingly soluble in water, methanol, ethanol and benzene while cold, and readily soluble in pyridine and methyl cellosolve while hot. The results of analyses were as follows:

| Elemental analysis | C | H | N |
|---|---|---|---|
| Calculated: | 64.60% | 5.92% | 13.72% |
| Found: | 64.24% | 5.71% | 13.15% |

Infrared absorption spectrum ($v_{cm^{-1}}^{KBr}$)
  1002 ($v$ C—O) ... first absorption
NMR spectrum of the HCl salt (CD$_3$OD solvent, δ)
  8.13, multiplet, 2H (ortho-protons of phenyl);
  7.84, multiplet, 3H (m- and p-protons of phenyl);
  4.90, singlet, H (—NH—); 4.62, singlet, 4H (—CH$_2$OH).

EXAMPLE 2

The procedure of Example 1 was repeated except that each of the catalysts tabulated below was used instead of potassium hydroxide. The results are also tabulated.

| Compound | Catalyst Amount (g) | (moles) | Amount yielded (g) | Yield (g) |
|---|---|---|---|---|
| NaOH | 4 | 0.1 | 37 | 90 |
| LiOH | 2.4 | 0.1 | 36 | 88 |
| K$_2$CO$_3$ | 13.8 | 0.1 | 29 | 71 |
| Na$_2$CO$_3$ | 10.6 | 0.1 | 31 | 74 |

EXAMPLE 3

Twenty nine grams (0.2 mole) of 2-phenylimidazole, 50 ml (0.6 mole) of 37% formalin, 100 ml of water and 4 g (0.1 mole) of sodium hydroxide were heated for 30 minutes with stirring in the same way, and post-treated in the same way as in Example 1 to afford 2-phenyl-4,5-dihydroxymethyl imidazole as a final product in an amount of 35.4 g (yield 86%).

EXAMPLE 4

Twenty nine grams (0.2 mole) of 2-phenylimidazole, 50 ml (0.6 mole) of 37% formalin, 50 ml of water and 5.6 g (0.1 mole) of potassium hydroxide were heated for 10 minutes in the same way as in Example 1 and post-treated in the same way as in Example 1 to afford 2-phenyl-4,5-dihydroxymethyl imidazole as a final product in an amount of 35.4 g (yield 86%).

EXAMPLE 5

Twenty nine grams (0.2 mole) of 2-phenylimidazole, 19 g (0.6 mole) of paraformaldehyde, 5.6 g (0.1 mole) of potassium hydroxide and 50 ml of ethanol were heated under reflux for 1.5 hours with stirring, cooled, and post-treated in the same way as in Example 1, to afford somewhat pale brown 2-phenyl-4,5-dihydroxymethyl imidazole as a final product in an amount of 37.8 g (yield 92%).

EXAMPLE 6

A reaction vessel equipped with a stirrer and a reflux condenser was charged with 15.8 g (0.1 mole) of 2-m-tolylimidazole, 24 ml (0.3 mole) of 37% formalin and 2 g (0.015 mole) of potassium carbonate. They were heated at about 90° C. for 1 hour with stirring. The contents were cooled, and the crystals were collected by filtration. The crystals collected were boiled together with 50 ml of water, cooled, and again collected by filtration. The crystals so collected were then boiled together with 20 ml of toluene, cooled, and collected by filtration. The crystals were recrystallized from methanol to afford 2-m-tolyl-4,5-dihydroxymethyl imidazole as a final product in an amount of 2 g (yield 9%). The thin-layer chromatography (Alumina G, ethanol) of these crystals gave only one spot at $R_f = 0.7$.

The product was of the following formula

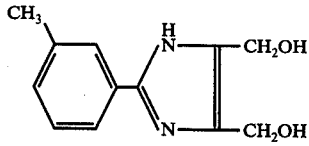

and had a melting point of 176° to 177.5° C. (methanol). It was basic, readily soluble in an aqueous solution of hydrochloric acid, sparingly soluble in water and toluene, and soluble in methanol. The results of analyses were as follows:

| Infrared absorption spectrum ($v_{cm^{-1}}^{KBr}$) |
| --- |
| 1010 ($vC$—O) |
| NMR spectrum (CD$_3$OD solvent, $\delta$) |
| 7.75–7.28, multiplet, 4H (phenyl protons); 4.66, singlet, 4H (—CH$_2$OH); 2.38, singlet, 3H (—CH$_3$) |
| Mass spectrum (m/e) |
| 218 (M$^+$), 201 (M$^+$—HO), 200 (M$^+$—H$_2$O), 184 (M$^+$-2(OH)), 91 (m-tolyl). |

EXAMPLE 7

A mixture of 15.8 g (0.1 mole) of 2-p-tolylimidazole, 24 ml (0.3 mole) of 37% formalin and 2 g of potassium hydroxide was heated for 30 minutes with stirring in the same way as in Example 1, and the reaction mixture was post-treated in the same way as in Example 1 except that methyl cellosolve was used instead of methanol as a recrystallization solvent to afford 2-p-tolyl-4,5-dihydroxymethyl imidazole as a final product in an amount of 2 g (yield 9%).

The product was of the following formula

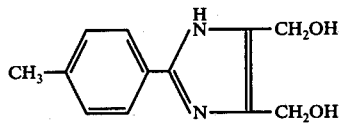

and had a melting point of 226° to 228° C. (methyl cellusolve). It was readily soluble in an aqueous solution of hydrochloric acid and methyl cellosolve, but sparingly soluble in water, methanol and toluene. The results of analyses were as follows:

| Infrared absorption spectrum ($v_{cm^{-1}}^{KBr}$) |
| --- |
| 1000 ($v$ C—O) ... first absorption |
| NMR spectrum (d$_6$-DMSO solvent, $\delta$) |
| 7.88, doublet, 2H (phenyl protons); 7.26, doublet, 2H (phenyl protons); 4.49, singlet, 4H (—CH$_2$OH); 2.32, singlet, 3H (—CH$_3$). |
| Mass spectrum (m/e) |
| 218 (M$^+$), 201 (M$^+$—HO), 200 (M$^+$—H$_2$O), 184 (M$^+$-2(OH)), 182 (M$^+$-2H$_2$O), 91 (p-tolyl). |

EXAMPLE 8

A mixture of 15.8 g (0.1 mole) of 2-p-tolyl imidazole, 9 g (0.3 mole) of paraformaldehyde, 2 g (0.015 mole) of potassium carbonate, and 50 ml of methyl cellosolve was heated at 95° C. for 30 minutes with stirring in the same way as in Example 1. 200 ml of water was added, and the reaction mixture was boiled for a while and cooled. The crystals were collected by filtration, boiled together with 20 ml of toluene, and cooled. The crystals were collected by filtration and recrystallized from methyl cellosolve to afford 2-p-tolyl-4,5-dihydroxymethyl imidazole as a final product in an amount of 4.5 g (yield 21%). The thin-layer chromatography (cellulose:n-BuOH:AcOH:W = 4:1:2) of the crystals gave only one spot at R$_f$ = 0.73.

EXAMPLE 9

A mixture of 15.8 g (0.1 mole) of 2-o-tolylimidazole 9 g (0.3 mole) of paraformaldehyde, 2 g (0.015 mole) of potassium carbonate and 50 ml of methyl cellosolve was heated at 90° C. for 30 minutes with stirring in the same way as in Example 1. Then, 200 ml of water was added, and the reaction mixture was boiled for a while and cooled. The crystals were collected by filtration, boiled together with 20 g of toluene, and collected by filtration. The crystals collected were dissolved in acetone, and a small amount of activated carbon was added. The mixture was filtered, and the filtrate was evaporated to dryness to afford 2-o-tolyl-4,5-dihydroxymethyl imidazole as a final product in an amount of 1 g (yield 5%). The thin-layer chromatography (alumina G, ethanol) of the crystals gave only one spot at R$_f$ = 0.6–0.8.

The product was of the following formula

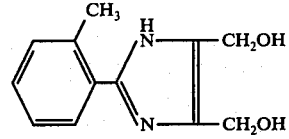

and had a melting point of 85° to 88° C. (methanol). It was basic, readily soluble in an aqueous solution of hydrochloric acid, sparingly soluble in water and toluene, and soluble in methanol and acetone. The results of analyses were as follows:

| Infrared absorption spectrum ($v_{cm^{-1}}^{KBr}$) |
| --- |
| 1015 ($vC$—O) |
| Mass spectrum (m/c) |
| 218 (M$^+$), 201 (M$^+$—OH), 200 (M$^+$—HO), 184 (M$^+$-2(OH)), 182 (M$^+$-2H$_2$O), 91 (o-tolyl). |

EXAMPLE 10

A reaction vessel equipped with a stirrer and a reflux condenser was charged with 32 g (0.2 mole) of 2-phenyl-4-methylimidazole, 25 ml (0.3 mole) of 37% formalin and 7 g (0.05 mole) of potassium carbonate. And they were heated to 100° C. with stirring. The contents instantly dissolved, and upon boiling which began after a while, crystals began to precipitate. After heating for 30 minutes, 100 ml of water was added to the reaction mixture, and the mixture was boiled for a while. Then, the crystals were collected by filtration, boiled together with 50 ml of methanol, cooled, and again collected by filtration. The crystals collected were immersed in 50 ml of cold methanol, collected by filtration, and dried to afford 2-phenyl-4(5)-methyl-5(4)-hydroxymethyl imidazole as a final product in an amount of 28.5 g (yield 76%). The thin-layer chromatography (silica G, ethanol) of these crystals gave only one spot at R$_f$ = 0.7.

The product was of the following formula

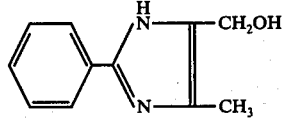

and had a melting point of 200.5° and 201.5° C. (decomp.) (methyl cellosolve). It was basic, soluble in an aqueous solution of hydrochloric acid, sparingly soluble in water, methanol, acetone and benzene while cold, and readily soluble in pyridine and methyl cellosolve while hot. The results of analyses were as follows:

| Elemental analysis values | | |
| --- | --- | --- |
| C | H | H |

-continued

| | | | |
|---|---|---|---|
| Calculated: | 70.19% | 6.43% | 14.88% |
| Found: | 70.08% | 6.50% | 14.86% |

Infrared absorption spectrum ($\nu_{cm^{-1}}^{KBr}$)
 1010 ($\nu$ C—O) . . . . . first absorption Mass spectrum (m/e)
 188 (M$^+$), 187, 171 (M$^+$—OH), 170, 129, 77 (phenyl)

NMR spectrum (CD$_3$OD solvent, $\delta$)
 7.84, multiplet, 2H (o-protons of phenyl);
 7.38, multiplet, 3H (m- and p-protons of phenyl);
 4.54, singlet, 2H (—CH$_2$OH); 2.25, singlet, 3H (—CH$_3$).

EXAMPLE 11

A mixture of 32 g (0.2 mole) of 2-phenyl-4-methyl imidazole, 25 ml (0.5 mole) of 37% formalin and 50 ml of water was heated under reflux for 30 minutes with stirring. The reaction mixture was cooled, and post-treated in the same way as in Example 10 to afford 2-phenyl-4(5)-methyl-5(4)-hydroxymethyl imidazole as a final product in an amount of 22.1 g (yield 59%).

EXAMPLE 12

A mixture of 32 g (0.2 mole) of 2-phenyl-4-methyl imidazole, 25 ml (0.3 mole) of 37% formalin, 50 ml of water, and 5 ml of a 40% aqueous solution of benzyl-trimethyl ammonium hydroxide was heated under reflux for 30 minutes with stirring. The reaction mixture was cooled, and post-treated in the same way as in Example 10 to afford 2-phenyl-4(5)-methyl-5(4)-hydroxymethyl imidazole as a final product in an amount of 25.9 g (yield 69%).

When the above procedure was repeated using 5 ml of triethalamine instead of the benzyl trimethyl ammonium hydroxide, the product was obtained in a yield of 69%.

EXAMPLE 13

A mixture of 46.8 g (0.2 mole) of 2-phenyl-4-benzylimidazole (which is a by-product resulting from the dehydrogenation of 2-phenylimidazoline to form 2-phenylimidazole), 25 ml (0.3 mole) of 37% formalin and 7 g (0.05 mole) of potassium carbonate was heated under reflux for 1 hour with stirring. The reaction mixture was cooled, and post-treated in the same way as in Example 10 to afford 2-phenyl-4(5)-benzyl-5(4)-hydroxymethyl imidazole as a final product in an amount of 33.3 g (yield 63%).

The product was of the following formula

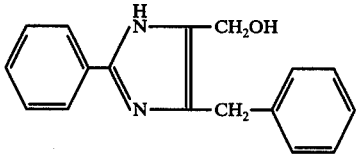

and had a melting point of 219° to 221° C. (decomp.) (methyl cellosolve). It was basic, soluble in an aqueous solution of hydrochloric acid, sparingly soluble in water, methanol, ethanol, acetone and benzene while cold, and soluble in pyridine and methyl cellosolve while hot. The results of analyses were as follows:

Elemental analysis values

| | C | H | N |
|---|---|---|---|
| Calculated: | 77.25% | 6.10% | 10.60% |
| Found: | 77.03% | 6.16% | 10.56% |

Infrared absorption analysis ($\nu_{cm^{-1}}^{KBr}$)
 1005 ($\nu$ C—O) . . . first absorption

EXAMPLE 14

A mixture of 34.4 g (0.2 mole) of 2-p-tolyl-4-methylimidazole, 25 ml (0.3 mole) of 37% formalin, 50 ml of water and 7 g (0.05 mole) of potassium carbonate was heated under reflux for 2.5 hours with stirring. The reaction mixture was cooled, and post-treated in the same way as in Example 10 to afford 2-p-tolyl-4(5)-methyl-5(4)-hydroxymethyl imidazole as a final product in an amount of 22.6 g (yield 56%).

The product was of the following formula

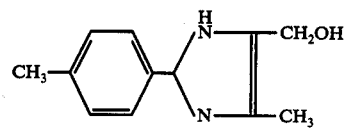

and had a melting point of 219° to 220° C. (decomp.) (methyl cellosolve). It was basic, readily soluble in an aqueous solution of hydrochloric acid, sparingly soluble in water, methanol, ethanol, acetone and benzene while cold, and soluble in pyridine and methyl cellosolve while hot. The results of analyses were as follows:

Elemental analysis values

| | C | H | N |
|---|---|---|---|
| Calculated: | 71.04% | 6.98% | 13.91% |
| Found | 71.29% | 7.05% | 13.84% |

Infrared absorption spectrum ($\nu_{cm^{-1}}^{KBr}$)
 1010 ($\nu$ C—O) . . . first absorption

EXAMPLE 15

The procedure of Example 14 was repeated except using 2-m-tolyl-4-methylimidazole as a starting material instead of 2-p-tolyl-4-methylimidazole, to afford 2-m-tolyl-4(5)-methyl-5(4)-hydroxymethyl imidazole as a final product.

The product was of the following formula

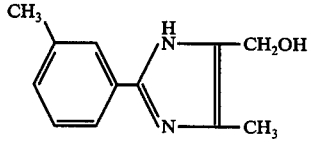

and had a melting point of 176° to 178° C. (decomp.). It was basic, readily soluble in an aqueous solution of hydrochloric acid, sparingly soluble in water, acetone and benzene while cold, and soluble in methanol, ethanol, pyridine and methyl cellosolve while hot. The results of analyses were as follows:

Elemental analysis values

| | C | H | N |
|---|---|---|---|
| Calculated: | 71.40% | 6.98% | 13.91% |
| Found: | 71.47% | 6.95% | 13.95% |

Infrared absorption spectrum ($\nu_{cm^{-1}}^{KBr}$)
 1000 ($\nu$ C—O) . . . first absorption

What we claimed is:
1. A compound of the formula
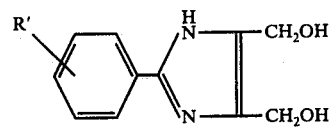
wherein R' represent a hydrogen atom or an alkyl group containing 1 to 4 carbon atoms.
* * * * *